United States Patent [19]

Law

[11] 4,062,946
[45] Dec. 13, 1977

[54] PARASITICIDAL ANIMAL DIP COMPOSITIONS PROTECTED AGAINST MICROBIAL BUILDUP

[75] Inventor: Andrew B. Law, Levittown, Pa.

[73] Assignee: Rohm and Haas Company, Philadelphia, Pa.

[21] Appl. No.: 190,298

[22] Filed: Oct. 18, 1971

[51] Int. Cl.$^2$ .................. A61K 33/36; A61K 31/555; A61K 31/425
[52] U.S. Cl. .................................. 424/134; 424/152; 424/203; 424/225; 424/245; 424/270
[58] Field of Search ............... 424/270, 245, 152, 134, 424/225, 203; 260/302 A

[56] References Cited

U.S. PATENT DOCUMENTS

| | | |
|---|---|---|
| 3,523,121 | 8/1970 | Lewis et al. ...................... 260/302 A |
| 3,544,580 | 12/1970 | Lewis et al. ...................... 260/302 A |
| 3,562,283 | 2/1971 | Lewis et al. ...................... 260/302 A |
| 3,635,997 | 1/1972 | Toepfl ............................. 260/302 A |

*Primary Examiner*—Sam Rosen
*Attorney, Agent, or Firm*—William E. Lambert, III

[57] ABSTRACT

Animal dip compositions which comprise a veterinary parasiticide and a carrier are protected against the buildup of microorganisms by the presence of a 2-alkyl-aryl- or aralkyl-3-isothiazolone or 3-hydroxyisothiazol or their salts with strong acids or their metal salt complexes.

25 Claims, No Drawings

PARASITICIDAL ANIMAL DIP COMPOSITIONS PROTECTED AGAINST MICROBIAL BUILDUP

This invention relates to animal dip compositions which are protected against the buildup of microorganisms and to methods for controlling the buildup of microorganisms in animal dip compositions.

Pesticidal animal dip solutions are often retained for periods up to 3 years before they are discarded. During this time they accumulate high concentrations of soil, feces, urine, hair, wool, and other impurities, which create a favorable environment for the growth of disease-causing and odor-producing microorganisms. As the microbial population increases, obnoxious odors develop and a potential for infection of the animals being dipped is created. The efficacy of certain of the parasiticides employed in such dips is also reduced through the microbial attack.

Most antimicrobial agents commmonly employed in various systems to prevent microbial buildup have been found to be ineffective as preservatives for animal dips, primarily because they are rapidly inactiviated by the high levels of organic matter which accumulate. Thus, animal dip preservatives which have improved resistance to inactivation by high concentrations of organic matter and which are effective for long periods of time at relatively low concentrations would be particularly desirable.

It has now been found that 3-isothiazolones, their salts with strong acids, and their complexes with metal ions are unexpectedly effective in preventing the buildup of microorganisms in animal dip compositions, even those containing high concentrations of organic matter. According to the invention, a parasiticidal animal dip protected against the buildup of microorganisms comprises a suitable veterinary parasiticide, an acceptable carrier, and a protectively effective amount of an isothiazolone of the formula

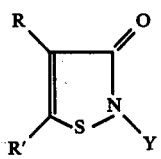

(I)

wherein
Y is a hydrogen atoms, a $(C_1-C_{18})$alkyl group, a $(C_2-C_4)$alkenyl or alkynyl group, a $(C_6-C_{10})$aryl group, or a $(C_7-C_{10})$aralkyl group,
R is a hydrogen atom, a halogen atom, or a $(C_1-C_4)$alkyl group,
R' is a hydrogen atom, a halogen atom, or a $(C_1-C_4)$alkyl group, or
R and R' can be taken together to complete a benzene ring, optionally substituted with one or more halogen atoms, nitro groups, $(C_1-C_4)$ alkyl groups, cyano groups, $(C_1-C_4)$alkoxy groups, or the like;
a salt of an isothiazolone of formula I with a strong inorganic or organic acid, such as hydrochloric acid, sulfuric acid, nitric acid, perchloric acid, p-toluene-sulfonic acid, hydrobromic acid, chlorosulfuric acid, chloroacetic acid, oxalic acid, maleic acid, succinic acid, or the like, or a metal salt complex of an isothiazolone having the formula

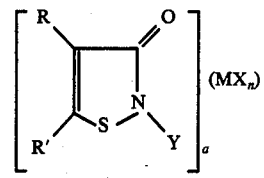

(II)

wherein
Y, R, and R' are as defined above,
M is a cation of a metal, such as barium, cadmium, calcium, chromium, cobalt, copper, iron, lead, lithium, manganese, mercury, nickel, sodium, silver, strontium, tin, zinc, or the like;
X is an anion forming a compound with the cation M, in which the compound has sufficient solubility to form a metal salt complex;
a is the integer 1 or 2; and
n is an integer which for the anion X satisfies the valence of the cation M.

The definition of Y above is intended to include both unsubstituted alkenyl, alkynyl, alkyl, aryl and aralkyl groups as well as such groups substituted with one or more halogen atoms, hydroxy groups, $(C_1-C_4)$alkoxy groups, $(C_1-C_4)$alkylamino or $(C_1-C_4)$ dialkylamino groups, nitro groups, cyano groups, carboxy groups, carb$(C_1-C_4)$alkoxy groups, or the like.

Representative Y substituents include hydrogen methyl, ethyl, propyl, isopropyl, butyl, hexyl, octyl, decyl, pentadecyl, octadecyl, cyclopropyl, cyclohexyl, benzyl, 3,4-dichlorobenzyl, 4-methoxybenzyl, 4-chlorobenzyl, 3,4-dichlorophenyl, hydroxymethyl, chloromethyl, chloropropyl, diethylaminoethyl, cyanoethyl, carbomethoxyethyl, ethoxyethyl, 2-methoxy-1-bromoethyl, 3,3,5-trimethylcyclohexyl, phenoxyethyl, p-chloroanilinomethyl, phenylcarbamoxymethyl, allyl, propynyl, vinyl, carboxyethyl, 1-isothiazolonylethyl, 1,2,2,-trichlorovinyl, and the like.

Representative R substitutents include hydrogen, bromine, chlorine, iodine, methyl, ethyl, propyl, butyl, and the like.

Representative R' substitutents are hydrogen, chlorine, bromine, iodine, methyl, ethyl, propyl, butyl, and the like.

The alkyl substituents represented by Y, R, and R' can have either branched- or straight-chain or cyclic spatial configuration.

Among the anions which X can represent are chloride, bromide, iodide, sulfate, nitrate, acetate, perchlorate, bisulfate, bicarbonate, oxalate, maleate, p-toluenesulfonate, carbonate, phosphate, and the like. The preferred metals from which M is derived are calcium, copper, magnesium, mangenese, nickel, and zinc. Among the metal cations embraced by M are cationic complexes of the metal ions, including complexes with ammonia, simple organic amines, and various heterocyclic organic amines such as pyridines, pyrimidines, and the like.

As used herein, the term 3-isothiazolones includes the tautomeric 3-hydroxy isothiazoles, where appropriate.

Typical 3-isothiazolones which are useful preservatives in the animal dip composition of the invention include the following:

3-isothiazolone (3-hydroxyisothiazole),
2-methyl-3-isothiazolone,
2-ethyl-3-isothiazolone, 2-propyl-3-isothiazolone,
2-butyl-3-isothiazolone,
2-octyl-3-isothiazolone,
2-decyl-3-isothiazolone,
2-octadecyl-3-isothiazolone,
2-cyclohexyl-3-isothiazolone,
4-chloro-2-methyl-3-isothiazolone,
4-bromo-2-methyl-3-isothiazolone,
5-chloro-2-methyl-3-isothiazolone,
5-chloro-2,4-dimethyl-3-isothiazolone,
4-bromo-5-chloro-2-methyl-3-isothiazolone,
4-bromo-2-cyclohexyl-3-isothiazolone,
4,5-dichloro-2-ethyl-3-isothiazolone,
4-methyl-2-octyl-3-isothiazolone,
4,5-dimethyl-2-octyl-3-isothiazolone,
2-benzyl-3-isothiazolone,
2-benzyl-4,5-dichloro-3-isothiazolone,
2-benzyl-5-chloro-3-isothiazolone,
2-(2,4-dichlorobenzyl)-3-isothiazolone,
2-(4methoxybenzyl)-3-isothiazolone,
2-(4-ethylbenzyl)-3-isothiazolone,
2-(3,4-dichlorophenyl)-3-isothiazolone,
2-(3,4-dichlorophenyl)-4-methyl-3-isothiazolone,
2-(2-cyanoethyl)-3-isothiazolone,
2-(2-carbomethoxyethyl)-3-isothiazolone,
2-carbomethoxymethyl-3-isothiazolone,
2-(2-ethoxyethyl)-3-isothiazolone,
2-(3,3,5-trimethylcyclohexyl)-3-isothiazolone,
2-(2-phenoxyethyl)-3-isothiazolone,
2-(2-methoxyethyl)-3-isothiazolone,
2-(3,4-dichloroanilinomethyl)-3-isothiazolone,
2-(4-chloroanilinomethyl)-3-isothiazolone,
2-(4-nitroanilinomethyl)-3-isothiazolone,
2-morpholinomethyl-3-isothiazolone,
2-piperidinomethyl-3-isothiazolone,
2-phenylcarbamoxymethyl-3-isothiazolone,
2-(3-chlorophenylcarbamoxymethyl)-3-isothiazolone,
2-(3,4-dichlorophenylcarbamoxymethyl)-3-isothiazolone,
2-allyl-3-isothiazolone,
2-propynyl-3-isothiazolone,
2-vinyl-3-isothiazolone,
5-chloro-2-vinyl-3-isothiazolone,
2-methoxymethyl-3-isothiazolone,
2-(2-carboxyethyl)-3-isothiazolone,
2-(2-carbobutoxyethyl)-3-isothiazolone,
2-[1-(N-pyrrolidonyl)ethyl]-3-isothiazolone,
2-[1-(N-isothiazolonyl)ethyl]-3-isothiazolone,
2-(1,2,2-trichlorovinyl)-3-isothiazolone,
2-(1-bromo-2-methoxyethyl)-3-isothiazolone,
2-(2-chloroethyl)-3-isothiazolone,
2-(3-chloropropyl)-3-isothiazolone,
2-cyclopropyl-3-isothiazolone,
2-[2-(4-chlorophenyl)ethyl]-3-isothiazolone,
2-hexyl-3-isothiazolone,
2-heptyl-3-isothiazolone,
2-cyclopentyl-3-isothiazolone,
2-(4-chlorophenyl)-3-isothiazolone,
2-(2,4-dichlorophenyl)-3-isothiazolone,
2-(2,3-dichlorophenyl)-3-isothiazolone,
2-(2,5-dichlorophenyl)-3-isothiazolone,
2-(3,4-dichlorophenyl)-3-isothiazolone,
2-(3-chlorophenyl)-3-isothiazolone,
2-phenyl-3-isothiazolone,
2-(2-clorophenyl)-3-isothiazolone,
2-pentyl-3-isothiazolone,
2-isopropyl-3-isothiazolone,
2-(2-hydroxyethyl)-3-isothiazolone,
2-(2-bromoethyl)-3-isothiazolone,
2-(1,2,2,2-tetrachloroethyl)-3-isothiazolone,
2-chloromethyl-3-isothiazolone,
2-(2-dimethylaminoethyl)-3-isothiazolone,
4,5-dichloro-2-octyl-3-isothiazolone,
4-chloro-2-octyl-3-isothiazolone,
4-bromo-2-octyl-3-isothiazolone,
4-bromo-2-(4-chlorophenyl)-3-isothiazolone,
4-bromo-2-butyl-3-isothiazolone,
2-(2,2,2-trichloro-1-hydroxyethyl)-3-isothiazolone,
2-(2,2,2-tribromo-1-hydroxyethyl)-3-isothiazolone
2-trichlorobenzyl-3-isothiazolone,
4-methyl-2-isopropyl-3-isothiazolone,
2-(4-methylphenyl)-3-isothiazolone,
2-hydroxymethyl-3-isothiazolone,
2-[2-(N,N-diethylamino)ethyl]-3-isothiazolone,
5-chloro-3-isothiazolone,
4-bromo-3-isothiazolone,
4-bromo-5-chloro-3-isothiazolone,
4-iodo-2-methyl-3-isothiazolone,
5-chloro-2-ethyl-3-isothiazolone,
4-bromo-5-chloro-2-ethyl-3-isothiazolone,
5-chloro-2-propyl-3-isothiazolone,
4-bromo-5-chloro-2-propyl-3-isothiazolones,
5-chloro-2-butyl-3-isothiazolone,
5-chloro-2-hexyl-3-isothiazolone,
5-chloro-2-octyl-3-isothiazolone,
4-bromo-5-chloro-2-octyl-3-isothiazolone,
5-chloro-2-decyl-3-isothiazolone,
5-chloro-2-dodecyl-3-isothiazolone,
5-chloro-2-phenyl-3-isothiazolone,
1,2-benzisothiazolone,
2-ethyl-1,2-benzisothiazolone,
2-butyl-1,2-benzisothiazolone,
2-butyl-5-bromo-1,2-benzisothiazolone,
2-pentyl-1,2-benzisothiazolone,
2-hexyl-5-methyl-1,2-benzisothiazolone,
2-t-octyl-1,2-benzisothiazolone,
2-t-octyl-6-ethoxy-1,2-benzisothiazolone,
2-nonyl-1,2-benzisothiazolone,
2-dodecyl-1,2-benzisothiazolone,
2-dodecyl-6-methyl-1,2-benzisothiazolone,
2-t-tridecyl-1,2-benzisothiazolone,
2-t-octadecyl-1,2-benzisothiazolone,
2-butyl-4-methyl-1,2-benzisothiazolone,
2-butyl-5-bromo-1,2-benzisothiazolone,
2-pentyl-4,6-dichloro-1,2-benzisothiazolone,
2-pentyl-6-methoxy-1,2-benzisothiazolone,
2-hexyl-5-methyl-1,2-benzisothiazolone,
2-isohexyl-4,5-diethyl-1,2-benzisothiazolone,
2-octyl-4-chloro-1,2-benzisothiazolone,
2-octyl-4,7-dichloro-1,2-benzisothiazolone,
2-t-octyl-6-chloro-1,2-benzisothiazolone,
2-t-octyl-6-ethoxy-1,2-benzisothiazolone,
2-nonyl-4-propoxy-1,2-benzisothiazolone,
2-dodecyl-4,6-dichloro-1,2-benzisothiazolone,
2-dodecyl-6-methyl-1,2-benzisothiazolone,
2-t-tridecyl-6-methyl-1,2-benzisothiazolone,
2-t-octadecyl-4,6-diethyl-1,2-benzisothiazolone,
2-p-n-butylphenyl-1,2-benzisothiazolone,
2-(2,4-dimethylphenyl)-1,2-benzisothiazolone,
2-(2,6-dimethylphenyl)-1,2-benzisothiazolone,
2-p-chlorophenyl-1,2-benzisothiazolone, and the like.

The salts of these 3-isothiazolones with strong acids and their metal salt complexes are also useful in the compositions of the invention.

The method of preparation of the isothiazolones and salts useful in the compositions of the invention is disclosed in United States patent application Ser. Nos. 841,548, filed on July 14, 1969, now U.S. Pat. No. 3,849,430 Ser. No. 836,660, filed on June 25, 1969, now U.S. Pat. No. 3,761,488 and Ser. No. 855,046, filed on Sept. 3, 1969, now abandoned and in U.S. Pat. No. 3,517,022, of Miller et al., granted on June 23, 1970. Generally, the isothiazolones of Formula I in which R and R' do not form a benzene ring are prepared by the oxidative cyclization of a disulfide-amide having the formula

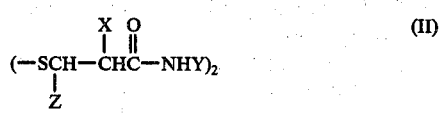

or, a mercapto-amide having the formula

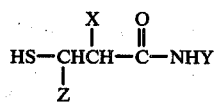

wherein X and Z are hydrogen or lower alkyl and Y is as defined above. The cyclization is accomplished by contacting the amide with a halogenating agent. Typical halogenating agents include chlorine, bromine, sulfuryl chloride, sulfuryl bromide, N-chlorosuccinimide, N-bromosuccinimide, and the like. Chlorine and sulfuryl chloride are the preferred halogenating agents. The benzisothiazolones of Formula I are prepared by the reaction of a primary amine with an o-halosulfenylbenzoyl halide or the intramolecular condensation of an o-halosulfenylbenzamide.

The method of preparation of the metal salt complexes useful in the compositions of the invention is described in United States patent application Ser. No. 142,775, of Miller et al., filed on May 12, 1971. Generally, this preparation involves the reaction of a 3-isothiazolone of Formula I with a metal salt of the formula $MX_n$, where M, X, and $n$ are as defined above, in solution or in slurry.

The 3-isothiazolone, salt, or complex can be added to the animal dip composition in any concentration which will effect the desired degree of protection against microorganism buildup. Generally, the concentration of the isothiazolone, the salt, or the complex in the animal dip will be about 10 to about 5000 parts per million by weight, and preferably about 25 to about 250 parts per million.

Any of the parasiticides, including insecticides or acaricides, which are used in dips for animals such as sheep, cattle, goats, and the like can be used in the compositions of the invention. Among the veterinary parasiticides which are commonly used are lindane, diazinon, O,O-diethyl O-3,5,6-trichloro-2-pyridyl phosphorothioate, toxaphene, coumaphos, magnesium fluosilicate, sodium arsenate, rotenone, O,O-diethyl O-(2,4-dichlorophenyl) phosphorothioate, O,O-diethyl O-3-chloro-4-methyl-1-oxo-2H-1-benzopyran-7-yl phosphorothioate, O,O-diethyl O-(4-methylthio-m-tolyl) phosphorothioate, and the like. The parasiticide can be present in any desired concentration, and the concentration will depend on the parasiticide used, the degree of protection needed, the parasites being controlled, the size of the dipping bath, the type of animal being treated, the number of animals to be treated, and other considerations. Generally, the concentration of the parasiticide will be about 50 to about 10,000 parts per million by weight, and preferably about 100 to about 2000 parts per million.

As used in this application, the term "animal dip" means compositions which contain a parasiticidal active ingredient and diluents or carriers, and which are adapted for mixing with water to produce stable aqueous compositions which are then applied to the animals to be treated either by dipping or by spraying, especially in a recycling spray apparatus. Any of the dip formulations commonly employed can be used in preparing the animal dip compositions of the invention, and the techniques for formulating these compositions, as well as the selection of suitable diluents and carriers and their proportions, are well known to those skilled in the art. Two of the most common types of formulation which are diluted with water to prepare the actual dip are wettable powder and emulsifiable concentrates.

A wettable powder will generally comprise a parasiticidal active ingredient and one or more dispersing agents, emulsifying agents, or wetting agents so that a stable aqueous dispersion of the active ingredient is formed on adding the powder to water. The active ingredient is generally in the form of very fine particles. A conventional solid inert diluent is often necessary, either as a grinding aid, for example, kaolin, or as an absorbent for the dispersing agent, for example, finely-divided silica. The proportion of dispersing agent to active ingredient is arranged so that on dilution with water a stable dispersion of the active ingredient is obtained. This is an essential feature of a wettable powder intended as a animal dip, in order that settling-out of the active ingredient in the dipping bath does not occur. The proportion of dispersing agent to active ingredient is also arranged so that passage of animals through the dipping bath does not result in excessive depletion of the active ingredient from the bath. The nature of the chosen dispersing agent is also important in connection with this latter feature, anionic or non-ionic agents generally being desirable. In most cases a wetting agent to ensure a rapid wetting of the powder so that dilution with water is facilitated. Non-toxic and non-irritant dispersing and wetting agents should be used. Such agents suitable for animal dips are well-known in the art. Typical examples are sulphite lye as a dispersing agent and a polyethylene oxide condensate of an alkylphenol as a wetting agent. Other wetting agents include polyoxyethylated derivatives of alkylphenols, fatty alcohols, fatty acids, and alkylamines, alkylarene sulfonates and dialkyl sulfosuccinates. Other dispersing agents include materials such as the sodium salt of the copolymer of maleic anhydride and an olefin such as diisobutylene, sodium lignin sulfonate and sodium formaldehydenaphthalene sulfonates.

An emulsifiable concentrate will generally comprise a parasiticidal active ingredient, one or more emulsifying agents, and a suitable water-immiscible solvent. Emulsifying agents suitable for use in animal dips are well-known in the art. It is frequently advantageous to employ two emulsifying agents, one favoring the oil phase and the other favoring the aqueous phase, as it is essential that, on dilution with water, a very stable emulsion is formed in order to avoid separation of the oil and aqueous phases. Manufactures of emulsifying agents frequently develop mixtures of, for example, an anionic and a non-ionic agent which are recommended for use in miscible liquids. Such a mixture may comprise a salt of an alkylbenzene sulphonic acid, for example, calcium dodecylbenzene-sulphonate and an ethylene oxide-alkylphenol condensate. The concentration of emulsifying agent(s) will be sufficient to ensure a stable emulsion. Non-toxic and non-irritant agents should be used. Solvents suitable for use in animal dips are well-known in the art, such as some of those available from coal and petroleum. The solvents should be non-toxic and non-irritant, for example, non-volatile, high boiling aromatic hydrocarbon fractions. Typical examples include heavy aromatic naphtha mixed methyl naphthalene fractions derived from coal, and kerosene. Mixed solvents may be used, isophorene and cyclohexanone being examples of well-known supplementary solvents used in minor quantities in admixtures with the aforementioned hydrocarbons. The light aromatic hydrocarbons such as benzene, toluene, xylene, and the like are generally not suitable for use in animal dips because of their irritant properties.

Animal dips as described above can also contain a bacteriostat in order to prevent infection in the animals due to the bacteria frequently found in dipping baths. For wettable copper sulfate or arsenic trioxide can be used. For emulsifiable concentrates, oil-soluble copper or zinc salts are suitable, for example copper or zinc naphthenate.

However, it has been found that the isothiazolones and their salts are also effective in controlling such bacterial infection as well as in preventing cross contamination during the treatment of the animals. Furthermore, the isothiazolones and their salts also control various microbial organisms in the dip which may cause discoloration and deterioration of sheep wool both on and off the animal. Included among the organisms that the isothiazolones have been found to control are *Erysipolethrix insidiosa*, cause of post-dipping lameness, *Corynebacterium ovis*, cause of lymphadentis in sheep and ulcerative lesions in cattle, and *Dermatophilus congolensis*, cause of dermatitis.

The following examples are set forth to illustrate further this invention but are not intended to limit it in any way.

100 ml. aliquots of the dip formulation being tested are placed in sterile four ounce glass bottles and to each 100 ml. aliquot is added a sufficient amount of one of the compounds being tested to provide the desired concentration. At "zero time," either 1 ml. or 10 ml. of an inoculum consisting of a homogenized slurry of sheep droppings, urine, and sheep wool plus added *Pseudomonas aeruginosa* and *Escherichia coli* organisms is added to each of the formulations being examined. Exactly 1 ml. aliquots of the inoculated test formulations are then removed after the indicated exposure times at 25° C and plated with Tryptone-Glucose-Extract Agar containing 0.05% sodium thioglycollate. The plates are incubated at ambient room temperature for 10 days and then are observed to determine the number of surviving organisms. In certain tests, as indicated, the test formulations are reinoculated after 20 days to determine the persistency of the compound tested as a preservative.

Three animal dip formulations are employed:

Formulation I — a solution of lindane at a concentration of 0.025% by weight of active ingredient in water.

Formulation II — as Formulation I, except in one-half strength nutrient broth (Difco Nutrient Broth) instead of water.

Formulation III — a solution of diazinon (formulated as a 50% wettable powder) at a concentration of 0.05% active ingredient in one-half strength nutrient broth (Difco Nutrient Broth).

The isothiazolones tested include:

A. 3-hydroxyisothiazole (3-isothiazolone)
B. 2-n-butyl-3-isothiazolone
C. 2-n-hexyl-3-isothiazolone
D. 2-n-octyl-3-isothiazolone
E. 5-chloro-2-methyl-3-isothiazolone hydrochloride
F. 5-chloro-2-methyl-3-isothiazolone calcium chloride complex (present in admixture with 2-methyl-3-isothiazolone calcium chloride complex)
G. 5-chloro-2-n-hexyl-3-isothiazolone.

Tables I to V summarize the results of these tests.

Table I

| Formulation | Isothiazolone | Conc. of Isothiazolone | Conc. of Inoculum | Time - Survival Test Number of Organisms Surviving/ml. of Test Solutions After Exposure of: | | | | | | |
|---|---|---|---|---|---|---|---|---|---|---|
| | | | | 1 Min. | 10 Min. | 30 Min. | 1 Hour | 2 Hours | 24 Hours | 5 Days |
| I | A | 5000 ppm | 10% | 110 | 0 | 0 | 0 | 0 | 0 | 0 |
| I | A | 1000 ppm | 10% | >1,000,000 | >1,000,000 | >1,000,000 | >1,000,000 | >500,000 | 10,000 | 7500 |
| I | B | 5000 ppm | 10% | >500,000 | >100,000 | >100,000 | 50,000 | 10,000 | 1,500 | 0 |
| I | B | 1000 ppm | 10% | >1,000,000 | >1,000,000 | >1,000,000 | >1,000,000 | 600,000 | 15,700 | 1450 |
| I | C | 5000 ppm | 10% | 8,250 | 2,665 | 1,850 | 1,300 | 750 | 500 | 420 |
| I | C | 1000 ppm | 10% | >1,000,000 | >1,000,000 | >1,000,000 | >500,000 | >100,000 | 8,000 | 650 |
| I | D | 5000 ppm | 10% | >500,000 | >100,000 | >10,000 | 1,000 | 275 | 150 | 100 |
| I | D | 1000 ppm | 10% | >500,000 | >100,000 | >10,000 | 2,250 | 1280 | 1350 | 1200 |
| I | None | | 10% | >10,000,000 | >10,000,000 | >10,000,000 | >10,000,000 | >10,000,000 | 3,600,900 | 900,000 |

EXAMPLE 1

To evaluate the isothiazolones as animal dip preservatives, the following "time survial" test procedure is employed.

Table II

| Formulation | Isothiazolone | Conc. of Isothiazolone | Conc. of Inoculum | Time - Survival Test Number of Organism Surviving/ml. of Test Solutions After Exposure of: | | | | |
|---|---|---|---|---|---|---|---|---|
| | | | | 10 Min. | 1 Hour | 2 Hours | 24 Hours | 5 Days |
| I | A | 5000 ppm | 1% | 0 | 0 | 0 | 0 | 0 |
| I | A | 2500 ppm | 1% | 1053 | 140 | 80 | 65 | 92 |
| I | A | 1000 ppm | 1% | 4250 | 535 | 285 | 126 | 118 |

Table II-continued

| Formulation | Isothiazolone | Conc. of Isothiazolone | Conc. of Inoculum | Time - Survival Test Number of Organism Surviving/ml. of Test Solutions After Exposure of: | | | | |
|---|---|---|---|---|---|---|---|---|
| | | | | 10 Min. | 1 Hour | 2 Hours | 24 Hours | 5 Days |
| I | D | 5000 ppm | 1% | 975 | 425 | 93 | 10 | 3 |
| I | D | 2500 ppm | 1% | >10,000 | 3340 | 2150 | 925 | 125 |
| I | D | 1000 ppm | 1% | >10,000 | 7560 | 2860 | 1560 | 261 |
| I | E | 5000 ppm | 1% | 0 | 0 | 0 | 0 | 0 |
| I | E | 2500 ppm | 1% | 253 | 165 | 52 | 30 | 53 |
| I | E | 1000 ppm | 1% | 1235 | 618 | 321 | 186 | 123 |
| I | G | 5000 ppm | 1% | 0 | 0 | 0 | 0 | 0 |
| I | G | 2500 ppm | 1% | 650 | 415 | 223 | 151 | 112 |
| I | G | 1000 ppm | 1% | — | — | — | — | — |
| I | None | — | 1% | >100,000 | 5275 | 3250 | 375 | 265 |
| * | None | — | 1% | 30,000,000 | >10,000,000 | >10,000,000 | 2,500,000 | 1,500,000 |

* no insecticide

Table III

| Formulation | Isothiazolone | Conc. of Isothiazolone | Conc. of Inoculum | Time - Survival Test Number of Organisms Surviving/ml. of Test Solutions After Exposure Of: | | | | |
|---|---|---|---|---|---|---|---|---|
| | | | | 1 Hour | 24 Hours | 10 Days | 20 Day | 40 Days* |
| II | A | 1000 ppm | 1% | 11,700 | 718 | 0 | 0 | |
| II | A | 500 ppm | 1% | >10,000 | 6265 | 2600 | 623 | 26 |
| II | A | 250 ppm | 1% | >100,000 | >10,000 | 7020 | 840 | 37 |
| II | A | 100 ppm | 1% | >100,000 | >100,000 | 14,000 | 927 | 52 |
| II | E | 1000 ppm | 1% | 5,360 | 3,000 | 500 | 86 | |
| II | E | 500 ppm | 1% | >10,000 | 8,650 | 2,000 | 425 | 27 |
| II | E | 250 ppm | 1% | >10,000 | >10,000 | 6,000 | 1200 | 31 |
| II | E | 100 ppm | 1% | >100,000 | >100,000 | 19,000 | 1830 | 40 |
| II | None | — | 1% | >100,000 | 163,000 | 16,000 | 15,300,000 | 32,500,000 |
| ** | None | — | 1% | 3,800,000 | 1,000,000 | 6,500,000 | 1,170,000,000 | >2,000,000,000 |

*Following the 20 day plating, all samples were reinoculated and then replated 20 days following this reinoculation.
**as II, with no insecticide.

Table IV

| Formulation | Isothiazolone | Conc. of Isothiazolone | Conc. of Inoculum | Time - Survival Test Number of Organisms Surviving/ml. of Test Solution After Exposure Of: | | |
|---|---|---|---|---|---|---|
| | | | | 10 Days | 20 Days | 40 Days* |
| III | A | 1000 ppm | 1% | 0 | 533 | 1850 |
| III | A | 500 ppm | 1% | 275 | 858 | 3015 |
| III | A | 250 ppm | 1% | 5,850 | 2,600 | >1,000,000 |
| III | A | 100 ppm | 1% | >100,000 | >100,000 | >1,000,000 |
| III | E | 1000 ppm | 1% | 0 | 230 | 2,435 |
| III | E | 500 ppm | 1% | 0 | 255 | 1,160 |
| III | E | 250 ppm | 1% | 0 | 1,885 | 1,715 |
| III | E | 100 ppm | 1% | 7,600 | 2,275 | 1,915 |
| III | None | — | 1% | 325,000,000 | 1,740,000,000 | 69,000,000 |
| ** | None | — | 1% | 760,000,000 | 1,200,000,000 | 72,000,000 |

*Following the 20 day plating, all samples were reinoculated and then replated 20 days following the reinoculation.
**As III, with no insecticide

Table V

| Formulation | Preservative | Conc. of Preservative in Dip Solution | Conc. of Inoculum | Time - Survival Test Number of Organisms Surviving/ml. of Test Solution After Exposure of: | | | |
|---|---|---|---|---|---|---|---|
| | | | | 1 Hour | 2 Weeks | 1 Month | 2 Months |
| III | None | — | 1% | 24,000,000 | 250,000,000 | 127,000,000 | 126,000,000 |
| III | Isothiazolone F | 200 ppm | 1% | 27,000,000 | 71,000 | 36,000 | 16,000 |
| III | Isothiazolone F | 100 ppm | 1% | 29,000,000 | 70,000 | 27,000 | 15,000 |
| III | Isothiazolone F | 75 ppm | 1% | 21,000,000 | 81,000 | 14,000 | 14,000 |
| III | Isothiazolone F | 50 ppm | 1% | 19,000,000 | 72,000 | 16,000 | 12,000 |
| III | Arsenic* | 100 ppm | 1% | 28,000,000 | 214,000,000 | 124,000,000 | 134,000,000 |

*Added as arsenic trioxide

The above data shows the effectiveness of the isothiazolones, their salts, and their metal salt complexes in controlling microbial buildup in animal dip compositions.

EXAMPLE 2

When evaluated according to the procedure of Example 1, the following isothiazolones show useful microbiocidal or microbiostatic properties in animal dip compositions:

5-chloro-3-isothiazolone
4-bromo-5-chloro-2-methyl-3-isothiazolone
5-methyl-3-isothiazolone
2-benzyl-3-isothiazolone
2-n-decyl-3-isothiazolone
2-(3,4-dichlorobenzyl)-3-isothiazolone
2-(2-bromoethyl)-3-isothiazolone hydrochloride
2-(4'-chlorophenyl)-3-isothiazolone
4,5-dichloro-2-phenyl-3-isothiazolone
5-chloro-2-vinyl-3-isothiazolone
2-(2-cyanoethyl)-3-isothiazolone
4-methyl-3-isothiazolone 5-chloro-2-methyl-3-isothiazolone zinc chloride complex
5-chloro-2-methyl-3-isothiazolone zinc acetate complex
2-benzyl-3-isothiazolone magnesium chloride complex
2-n-octyl-3-isothiazolone calcium chloride complex
5-chloro-2-n-octyl-3-isothiazolone zinc chloride complex
5-chloro-2-methyl-3-isothiazolone cupric chloride complex
3-isothiazolone magnesium chloride complex
4-bromo-5-chloro-2-methyl-3-isothiazolone calcium chloride complex

EXAMPLE 3

To evaluate the effectiveness of the isothiazolones in controlling pathogenic bacteria in animal dip compositions, the following tests are used.

Samples of wool are dipped in water containing a bacteriostatic agents at several concentrations. After allowing the wool to dry for 24 hours the number of microorganisms still viable in the wool and in the solution of the bacteriostatic agent is determined. In another test, aliquots of nutrient broth containing several dilutions of the bacteriostatic agents is innoculated with six species of bacteria found in wool and as pathogens on sheep. The broths are examined for growth of the organism at intervals up to seven days.

The isothiazolones tested as bacteriostatic agents include 3-isothiazolone (3-hydroxyisothiazole) and 5-chloro-2-methyl-3-isothiazolone. Sodium arsenate is also evaluated in these tests as a standard.

In the first test, the following procedure is employed:

Solutions of the tested bacteriostats at concentrations of 10,000, and 1000 parts per million (by weight) are used, controls of sterile water were included. Arsenic and 3-isothiazolone are dissolved in sterile water, and 5-chloro-2-methyl-3-isothiazolone in 10 ml of acetone and diluted with distilled water to give the required concentration.

Wool samples are taken from the side of Corriedale, Merino and Crossbred fleeces. Samples of wool 5.0g in weight are immersed for 2 minutes in beakers containing 130 ml of the bacteriostatic solutions, and stirred with a sterile glass rod. At the end of this time, the wool is taken from the beakers, drained to remove the free water and dried at 32° C for 24 hours.

Sub-samples each of 1.0g are then shaken with glass beads in sterile water blanks. The number of microorganisms per gram of wool is determined, using standard dilution plate count techniques.

After the wool has been removed, the solutions are held at room temperature for 7 days and the number of organisms they contain is determined.

The numbers of microorganisms per gram of wool dipped in bacteriostat solutions, compared with those in wool dipped in sterile water only, are given in Table VI.

The number of organisms per ml of the bacteriostat solution one week after dipping, compared with water, are give in Table VII.

TABLE VI

| Bacteriostat | Concentration ppm | Corriedale (a) | Corriedale (b) | Crossbred | Merino |
|---|---|---|---|---|---|
| Arsenic | 10 | .24 | .01 | .08 | 31 |
|  | 100 | .3 | .006 | .03 | 12.5 |
|  | 1000 | .2 |  | .009 | 0.2 |
| 5-methyl-2-chloro-3-isothiazolone | 10 | .2 | .45 | .18 | 63 |
|  | 100 | .06 | .8 | .06 | 12 |
|  | 1000 | .15 | .002 | .0009 | .04 |
| 3-isothiazolone | 10 | .37 | .9 | .81 | 34 |
|  | 100 | .009 | .09 | .47 | 2.8 |
|  | 1000 | .06 | .004 |  | .29 |

TABLE VII

| Bacteriostat | Concentration ppm | Corriedale (a) | Corriedale (b) | Crossbred | Merino |
|---|---|---|---|---|---|
| Arsenic | 10 | 2.3 | 280 | .48 | .06 |
|  | 100 | 5.2 | 260 | 1.8 | .09 |
|  | 1000 | .12 | 720 | .9 | 1 |
| 5-chloro-2-methyl-3-isothiazolone | 10 |  | 2.8 | .008 | .002 |
|  | 100 |  | .55 | .0001 | .007 |
|  | 1000 | .0004 | .012 | .0002 | .0002 |
| 3-isothiazolone | 10 | 1.1 | .002 | 3.25 |  |
|  | 100 | .01 | .002 | .07 | 16.5 |
|  | 1000 |  | .004 | .0002 | .005 |

In the second test, the following procedure is employed: Bottles containing brain.heart infusion (BHI) broth (Difco) are inoculated with *Pseudomonas aeruginosa, Escherichia coli* and *E. coli, $H_2S$ producing,* which were incubated for three days at 32° C; *Dermatophilus congolensis, Erysipelothrix insidiosa* and *Corynebacterium ovis,* incubated for 6 days.

Using a hypodermic syringe 0.5 ml aliquots of these cultures are inoculated by syringe into bottles containing 10 ml of BHI broth to which has been added different dilutions of the bacteriostatic agents. The inoculated broths are incubated at 32° C, and checked for growth of the organism after 1, 3 and 7 days.

Growth is checked by observing cloudiness when inoculated and sterile control tubes were compared. The survival of the organisms was assessed by streaking a loopful of broth on to BHI agar and observing the presence of colonies.

Tables VIII to X summarize the results of these tests.

TABLE VIII

BACTERIOSTATIC EFFECT OF 5-CHLORO-2-METHYL-3-ISOTHIAZOLONE (minimum bacteriostatic concentration, ppm)

| Bacteria | Growth After | | |
|---|---|---|---|
|  | 1 Day | 3 Days | 5 Days |
| *Pseud.* | 100 | 100 | 100 |
| *E. coli.* | 10 | 100 | 100 |
| *E. coli.* ($H_2S$ prod.) | 100 | 100 | 100 |

TABLE VIII-continued
BACTERIOSTATIC EFFECT OF 5-CHLORO-2-METHYL-3-ISOTHIAZOLONE
(minimum bacteriostatic concentration, ppm)

| Bacteria | Growth After | | |
|---|---|---|---|
| | 1 Day | 3 Days | 5 Days |
| Derm. | 10 | 100 | 100 |
| Erysi. | 10 | 100 | 100 |
| Coryne | 10 | 100 | 100 |

TABLE IX
BACTERIOSTATIC EFFECT OF 3-ISOTHIAZOLONE
(minimum bacteriostatic concentration, ppm)

| Bacteria | Growth After | | |
|---|---|---|---|
| | 1 Day | 3 Days | 5 Days |
| Pseud. | 100 | 500 | 500 |
| E. coli. | 100 | 100 | 100 |
| E. coli. (H$_2$S prod.) | 100 | 500 | 500 |
| Derm. | 10 | 100 | 100 |
| Erysi. | 10 | 100 | 100 |
| Coryne. | 1 | 10 | 100 |

TABLE X
BACTERIOSTATIC EFFECT OF SODIUM ARSENATE
(minimum bacteriostatic concentration, ppm)

| Bacteria | Growth after | | |
|---|---|---|---|
| | 1 Day | 3 Days | 5 Days |
| Pseud. | 500 | 800 | 800 |
| E. coli | 500 | 800 | 800 |
| E. coli. (H$_2$S prod.) | 80 | 800 | 800 |
| Derm. | 0.8 | 8 | 80 |
| Erysi. | 8 | 8 | 8 |
| Coryne. | 0.08 | 8 | 8 |

The above data shows the effectiveness of isothiazolones in controlling bacteria which can cause disease in sheep or discoloration of wool. The isothiazolones, their salts, and their metal salt complexes can also be used to effect useful control of other bacteria which can cause disease in animals, especially those which can grow in or be transmitted through animal dip compositions. When other isothiazolones of Formula I, and their salts and complexes, including those of Examples 1 and 2, are tested by the procedures described above, beneficial bacteriostatic results are obtained.

It is to be understood that changes and variations may be made without departing from the spirit and scope of the invention as defined by the appended claims.

I claim:

1. An animal dip composition protected against the buildup of microorganisms which comprises a veterinary animal dip parasiticide, an acceptable carrier, and an effective amount of a compound of the formula

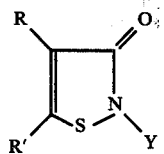

wherein
Y is a hydrogen atom, a (C$_1$-C$_{18}$)alkyl group, a (C$_6$-C$_{10}$)aryl group, or a (C$_7$-C$_{10}$)aralkyl group,
R is a hydrogen atom, a halogen atom, or a (C$_1$-C$_4$)alkyl group,
R' is a hydrogen atom, a halogen, or a (C$_1$-C$_4$)alkyl group, or
R and R' can be taken together to complete a benzene ring, optionally substituted with one or more halogen atoms, nitro groups, (C$_1$-C$_4$)alkyl groups, cyano groups, or (C$_1$-C$_4$)alkoxy groups;
a salt of a compound of formula I with a strong inorganic or organic acid, or a metal salt complex of an isothiazolone having the formula

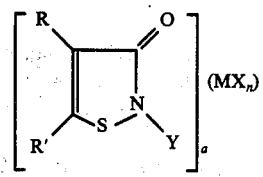

wherein
Y, R, and R' are as defined above,
M is a cation of barium, calcium, lithium, magnesium, sodium or strontium;
X is an anion forming a compound with the cation M, in which the compound has sufficient solubility to form a complex of the invention;
$a$ is the integer 1 or 2; and
$n$ is an integer which for the anion X satisfies the valence of the cation M.

2. A composition according to claim 1 which comprises a veterinary parasiticide, an acceptable carrier, and an effective amount of a compound of formula I.

3. A composition according to claim 2 wherein Y is a (C$_1$-C$_{18}$)alkyl group.

4. A composition according to claim 3 wherein R is a hydrogen atom and R' is a halogen atom.

5. A composition according to claim 4 wherein Y is a methyl group and R' is a chlorine atom.

6. A composition according to claim 3 wherein R is a hydrogen atom and R' is a hydrogen atom.

7. A composition according to claim 6 wherein Y is a n-octyl group.

8. A composition according to claim 1 which comprises a veterinary parasiticide, an acceptable carrier, and an effective amount of a salt of a compound of formula I with a strong inorganic or organic acid.

9. A composition according to claim 1 which comprises a veterinary parasiticide, an acceptable carrier, and an effective amount of a metal salt complex of formula II.

10. A composition according to claim 9 wherein Y is a (C$_1$-C$_{18}$)alkyl group.

11. A composition according to claim 10 wherein R is a hydrogen atom and R' is a halogen atom.

12. A composition according to claim 11 wherein Y is a methyl group and R' is a chlorine atom.

13. A composition according to claim 12 wherein MX is a calcium chloride.

14. A composition according to claim 1 wherein the microorganisms are bacteria or fungi.

15. A composition according to claim 1 wherein the microorganisms are pathogenic bacteria.

16. A method of controlling microorganisms in a veterinary parasiticidal animal dip composition containing a veterinary parasiticide which comprises adding to the dip composition an effective amount of a compound of the formula

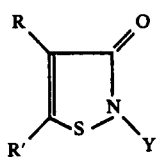

(I)

wherein
Y is a hydrogen atom, a $(C_1-C_{18})$alkyl group, a $(C_6-C_{10})$aryl group, or a $(C_7-C_{10})$aralkyl group,
R is a hydrogen atom, a halogen atom, or a $(C_1-C_4)$alkyl group,
R' is a hydrogen atom, a halogen, or a $(C_1-C_4)$alkyl group, or
R and R' can be taken together to complete a benzene ring, optionally substituted with one or more halogen atoms, nitro groups, $(C_1-C_4)$alkyl groups, cyano groups, or $(C_1-C_4)$alkoxy groups;
a salt of a compound of formula I with a strong inorganic or organic acid, or a metal salt complex of an isothiazolone having the formula

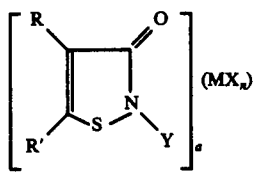

(II)

wherein
Y, R, and R' are as defined above,
M is a cation of barium, calcium, lithium, magnesium sodium or strontium;
X is an anion forming a compound with the cation M, in which the compound has sufficient solubility to form a complex of the invention;
a is the integer 1 or 2; and
n is an integer which for the anion X satisfies the valence of the cation M.

17. A method according to claim 16 which comprises adding an effective amount of a compound of formula I.

18. A method according to claim 17 wherein Y is a $(C_1-C_{18})$alkyl group.

19. A method according to claim 18 wherein Y is 2-n-octyl-3-isothiazolone.

20. A method according to claim 16 which comprises adding an effective amount of a salt of a compound of formula I with a strong inorganic or organic acid.

21. A method according to claim 16 which comprises adding an effective amount of a metal salt complex of formula II.

22. A method according to claim 21 wherein the metal salt complex is a calcium chloride complex of 5-chloro-2-methyl-3-isothiazolone.

23. A method according to claim 16 wherein the organisms are bacteria or fungi.

24. A method according to claim 16 wherein the organisms are pathogenic bacteria.

25. A method of preventing bacterial and fungal cross-contamination of animals during treatment of the animals with a veterinary parasiticidal animal dip composition containing a veterinary parasiticide which comprises adding to the dip composition an effective amount of a compound of the formula

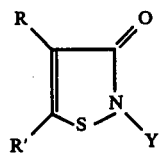

(I)

wherein
Y is a hydrogen atom, a $(C_1-C_{18})$alkyl group, a $(C_6-C_{10})$aryl group, or a $(C_7-C_{10})$aralkyl group,
R is a hydrogen atom, a halogen atom, or a $(C_1-C_4)$alkyl group,
R' is a hydrogen atom, a halogen, or a $(C_1-C_4)$alkyl group, or
R and R' can be taken together to complete a benzene ring, optionally substituted with one or more halogen atoms, nitro groups, $(C_1-C_4)$alkyl groups, cyano groups, or $(C_1-C_4)$alkoxy groups;
a salt of a compound of formula I with a strong inorganic or organic acid, or a metal salt complex of an isothiazolone having the formula

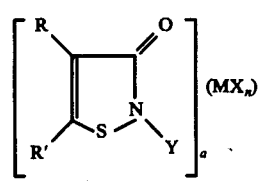

(II)

wherein
Y, R, and R' are as defined above,
M is a cation of barium, calcium, lithium, magnesium, sodium or strontium;
X is an anion forming a compound with the cation M, in which the compound has sufficient solubility to form a complex of the invention;
a is the integer 1 or 2; and
n is an integer which for the anion X satisfies the valence of the cation M.

* * * * *